US006610679B2

(12) United States Patent
Miller et al.

(10) Patent No.: US 6,610,679 B2
(45) Date of Patent: *Aug. 26, 2003

(54) USE OF GREEN PORPHYRINS TO TREAT NEOVASCULATURE IN THE EYE

(75) Inventors: Joan W. Miller, Winchester, MA (US); Evangelos S. Gragoudas, Lexington, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/824,155

(22) Filed: Apr. 2, 2001

(65) Prior Publication Data

US 2001/0023247 A1 Sep. 20, 2001

Related U.S. Application Data

(63) Continuation of application No. 09/347,382, filed on Jul. 6, 1999, now Pat. No. 6,225,303, which is a continuation of application No. 08/942,475, filed on Oct. 2, 1997, now abandoned, which is a continuation of application No. 08/390,591, filed on Feb. 17, 1995, now Pat. No. 5,798,349, which is a continuation-in-part of application No. 08/209,473, filed on Mar. 14, 1994, now Pat. No. 5,707,986.

(51) Int. Cl.$^7$ ............................................. A61K 31/555

(52) U.S. Cl. ..................... 514/185; 514/410; 514/912

(58) Field of Search ................................ 514/185, 410, 514/912

(56) References Cited

U.S. PATENT DOCUMENTS

| | | | |
|---|---|---|---|
| 4,883,790 A | 11/1989 | Levy et al. | 540/145 |
| 4,920,143 A | 4/1990 | Levy et al. | 514/410 |
| 5,087,636 A | 2/1992 | Jamieson et al. | 514/410 |
| 5,171,749 A | 12/1992 | Levy et al. | 514/410 |
| 5,214,036 A | 5/1993 | Allison et al. | 514/185 |
| 5,283,255 A | 2/1994 | Levy et al. | 514/410 |
| 5,705,518 A | 1/1998 | Richter et al. | 514/410 |
| 5,770,619 A | 6/1998 | Richter et al. | 514/410 |
| 5,798,349 A | 8/1998 | Levy et al. | 514/185 |

OTHER PUBLICATIONS

1989 Academy Poster Abstract and Retina/Macula Society Abstract, Bates Nos. KLI129–KLI131.
Combined Meeting of The Macula Society and Retina Society, Program and Abstract (1989), Bates Nos. KLI197–KLI199.
The Annual Ophthalmology Clinical and Scientific Meeting, Program (1990), Bates Nos. KLI200–KLI203.
Phacoemulsification and Small Incision Cataract Implant Surgery, Agenda (1990), Bates Nos. KLI204–KLI206.
The Annual Ophthalmology Clinical and Scientific Meeting, Program (1990), Bates Nos. KLI218–KLI221.

Gomer et al. "Hematoporphyrin Derivative Photoradiation Induced Damage to Normal and Tumor Tissue of the Pigmented Rabbit Eye" *Eye Research* 3: 229–237.
Schmidt–Erfurth et al., "Photodynamic Therapy of Experimental Choroidal Melanoma Using Lipoprotein–delivery Benzoporphyrin," *Ophthalmology* (1994) 101:89–99.
Schmidt–Erfurth et al., "Vascular Targeting in Photodynamic Occlusion of Subretinal Vessels," *Ophthalmology* (1994) 101:1953–1961.
Schmidt–Erfurth et al., "In Vivo Uptake of Liposomal Benzoporphyrin Derivative and Photothrombosis in Experimental Corneal Neovascularization," *Lasers in Surgery and Medicine* (1995) 17: 178–188.
Kliman et al., "Retinal and Choroidal Vessel Closure Using Phthalocyanine Photodynamic Therapy," *Lasers in Surgery and Medicine* (1994) 15:11–18.
Kliman et al., "Phthalocyanine Photodynamic Therapy: New Strategy for Closure of Choroidal Neovaculization," Lasers in Surgery and Medicine (1994) 15:2–10.
Allison et al, "The Effects of Plasma Lipoproteins on in vitro Tumor Cell Killing and in vitro Tumor Photosensitization with Benzoporphyrin Derivative," (1991) 54(5):709–715.
Poster corresponding to Abstract 2294 *Investigative Ophthalmology and Visual Science* (1993) 34:1169.
Haimovici et al., "Localization of Benzoporphyrin Derivative Monoacid in the Rabbit Eye," *Investigative Opthalmology and Visual Science*, (1993) 34:1303 Abstract 2955.
Lin et al., "Measurement of BPD Photosensitizer Kinetics in Retinal and Choroidal Vessels by Fluorescence Imaging," *Investigative Opthalmology and Visual Science* (1993) vol. 34, p. 1168, Abstract No. 2293.
Lin et al., "Photodynamic Closure of Choroidal Vessels Using Benzoporphyrin Derivative," *Investigative Opthalmology and Visual Science* (1993) 34:1303 Abstract 2953.
Moulton et al., "Response of Retinal and Choroidal Vessels to Photodynamic Therapy Using Benzoporphyrin Derivative Monoacid," *Investigative Opthalmology and Visual Science* (1993) 34:1169 Abstract 2294.
Pandey et al., "Efficient Synthesis of New Classes of Regiochemically Pure Benzoporphyrin Derivatives," *Bioorganic & Medicinal Chemistry Letters* (3) 12:2615–2618 (1993).
Schmidt–Erfuth et al., "Photothrombosis of Ocular Neovascularization Using Benzoporphyrin (BPD)," *Investigative Opthalmology and Visual Science* (1993) 34:1303 Abstracts 2956.

(List continued on next page.)

*Primary Examiner*—Zohreh Fay
(74) *Attorney, Agent, or Firm*—Testa, Hurwitz & Thibeault, LLP

(57) ABSTRACT

Photodynamic therapy of conditions of the eye characterized by unwanted neovasculature, such as age-related macular degeneration, is effective using green porphyrins as photoactive agents, preferably as liposomal compositions.

6 Claims, 1 Drawing Sheet

OTHER PUBLICATIONS

Schmidt–Erfurth et al., "Photodynamic Therapy of Experimental Melanoma Using Lipoprotein–Delivered Benzoporphyrin," *Opthalmology* (1994) 101(1):89–99.

Schmidt et al., "Photosensitizing Potency of Benzoporphyrin Derivative (BPD) Associated with Human Low Density Lipoprotein (LDL)," *Investigative Opthalmology and Visual Science* (1992) 33:1253 Abstract 2802.

Walsh et al., "Photodynamic Therapy of Experimental Choroidal Neovascularization Using Benzoporphyrin Derivative Monoacid," *Investigative Opthalmology and Visual Science* (1993) 34:1303 Abstracts 2954.

Richter et al., "Characterization of Benzoporphyrin Derivative, A New Photosensitizer," *SPIE* 97 (Advances in Photochemotherapy), 132–138 (1988).

Kessel, D., "Photosensitization With a Benzoporphyrin Derivative," *Photochemistry and Photobiology* (1989) 49(5):579–582.

Richter et al., "in Vitro Evaluation of Phototoxic Properties of Four Structurally Benzoporphyrin Derivatives," *Photochemistry and Photobiology*, (1990) 52(3):495–500.

Allison et al., "The Effect of Low Density Lepoprotein Association With Benzoporphyrin Derivative on Photodynamic Therapy," *Photochemistry and Photobiology*, (1991) 53(Suppl), 95S.

Howard et al., "Photodynamic Therapy (PDT) or Pigmented Choroidal Melanoma Using a Liposomal Preparation of Benzoporphyrin Derivative (BPD)," *Investigative Opthalmology and Visual Science* (1994) 35(4): 1722.

Kramer et al., "Photodynamic Therapy (PDT) of Experimental Choroidal Neovascularization (CNV) Using Liposomal Benzoporphyrin Derivative Monoacid (BPD–MA): Refinement of Dosimetry," *Investigative Opthalmology and Visual Science* (1994) 35(4):1503.

Lui et al., "Photodynamic Therapy of Malignant Skin Tumors in Humans With Benzoporphyrin Derivative and 690 NM Laser Light," *J. of Invest. Dermatol.* (1994) 102(4):569.

Schmidt–Erfurth et al., "Vascular Targeting in Photodynamic Occlusion of Subretinal Vessels," *Opthalmology* (1994) 101:1953–1961.

Gomer et al., "Hematoporphyrin Derivative Photoradiation Therapy for the Treatment of Intraocular Tumors: Examination of Acute Normal Ocular Tissue Toxicity," *Cancer Research* (1983) 43:721–727.

Bruce, "Photoradiation for Choroidal Malignant Melanoma," *Porphyrins in Tumor Phototherapy* (1984) ed. by Andreoni and Cubbeddu, Plenum Press, New York, NY, pp. 455–461.

Lui et al., "Photodynamic Therapy Induced Choroidal Vessel Destruction for the Treatment of Ocular Melanoma," *Investigative Opthalmology and Visual Science* (1987) 28 (3, Supp.).

Murphee et al., "The Evolution of Photodynamic Therapy Techniques in the Treatment of Intracular Tumors," *Photochemistry and Photobiology* (1987) 46(5):919–923.

Fish et al., "Photodynamic Therapy of Conjunctival Melanoma in Rabbits: Toxicity and Dose Response," *Investigative Opthalmology and Visual Science* (1988) 29(Abstr. Issue): 341.

Ben–Hur et al., "Photodynamic Therapy of Age–Related Macular Degeneration and Atherosclerosis," *Ber. Bunsenges. Phys. Chem.* (1989) 93:284–286.

Gomer, "Photodynamic Therapy in the Treatment of Malignancies," *Semin. Hematol.* (1989) 26(1):2734.

Kliman et al., "Angiography and Photodynamic Therapy of Experimental Choroidal Neovascularization using Phthalocyanin Dye," *Investigative Opthalmology and Visual Science* (1989) 30(3,Supp) 371.

Lingua et al., "Photodynamic Therapy for Ocular Tumors," *J. Photochem. Photobiol. B.* (1991) 9(1):199–122.

Ozler et al., "Photodynamic Therapy of Experimental Subchoroidal Melanoma Using Chloroaluminum Sulfonated Phthalocyaninc," *Arch Opthalmol.* (1992) 100:555–561.

Hisazumi et al., "Photodynamic Therapy of Superficial Tumors and Carcinomas In Situ of the Bladder," *Gan No Rinsho* (1985) 31 (6, Suppl.), Abstract.

Masaki et al., "Photodynamic Therapy of Superficial Bladder Tumors," *Hinyokika Kiyo* (1986) 32(12):1941–1948.

Bachor et al., "Comparision of Intravenous and Intravesical Administration of Chloro–Aluminum Sulfonated Phthalocyanine for Photodynamic Treatment in a Rat Bladder Cancer Model," *J. of Urology* (1992) 147:1404–1410.

Morgan et al., "Second Generation Photosensitizers for Photodynamic Therapy," *Photochem. Photobiol.* (1991) 53(Suppl.) 103S.

Morgan et al., "Diels–Alder Adducts of Vinyl Porphyrins: Synthesis and In vivo Photodynamic Effect Against a Rat Bladder Tumor," *J. Med. Chem.* (1990) 33:1258–1262.

Richter et al., "Photosensitizing Potency of Structural Analogues of Benzoporphyrin Derivative (BPD) in a Mouse Tumour Model," *Br. J. Cancer* (1991) 63:87–93.

McCaughan, Jr., "Overview of Experiences With Photodynamic Therapy for Malignancy in 192 Patients," *Photochemistry and Photobiology* (1987) 46(5):903–909.

Ferrario et al., "Systemic Toxicity in Mice Induced by Localized Porphyrin Photodynamic Therapy," *Cancer Research* (1990) 50:539–543.

Friedman et al., "The Retinal Pigment Epithelium," *Arch. Ophthal.* (1968) 80:265–279.

Thomas et al., "Closure of Experimental Subretinal Neovascular Vessels with Dihematoporphyrin Ether Augmented Argon Green Laser Photocoagulation," *Photocoagulation* (1987) 881–886.

Lui et al., "Photodynamic Therapy in Dermatology: Recent Developments," *Dermatologic Therapy* (1993) 11:1–13.

Moan et al., "Photochemotherapy of Cancer: Experimental Research," *Photochemistry and Photobiology* (1992) 55:931–948.

Kessel, D., "Porphyrin–Lipoprotein Association As a Factor In Porphyrin Localization," *Cancer Letters* (1986) 33:183–188.

USE OF GREEN PORPHYRINS TO TREAT NEOVASCULATURE IN THE EYE

This application is a continuation of U.S. Ser. No. 09/347,382, filed Jul. 6, 1999, now U S. Pat. No. 6,225,303 B1, which is a continuation of U.S. Ser. No. 08/942,475, filed Oct. 2, 1997, now abandoned, which is a continuation of U.S. Ser. No. 08/390,591, filed Feb. 17, 1995, now U.S. Pat. No. 5,798,349, which is a continuation-in-part of U.S. Ser. No. 08/209,473, filed Mar. 14, 1994, now U.S. Pat. No. 5,707,986, the disclosures of which are incorporated herein by reference.

TECHNICAL FIELD

The invention is in the field of photodynamic therapy, specifically related to ocular conditions. More particularly, the invention concerns the use of green porphyrins in photodynamic therapeutic treatment of conditions characterized by unwanted neovasculature in the eye.

BACKGROUND ART

Choroidal neovascularization leads to hemorrhage and fibrosis, with resultant visual loss in a number of eye diseases, including macular degeneration, ocular histoplasmosis syndrome, myopia, and inflammatory diseases. Age-related macular degeneration (AMD) is the leading cause of new blindness in the elderly, and choroidal neovascularization is responsible for 80% of the severe visual loss in patients with this diseases. Although the natural history of the disease is eventual quiescence and regression of the neovascularization process, this usually occurs at the cost of sub-retinal fibrosis and vision loss.

Current treatment of AMD relies on occlusion of the blood vessels using laser photocoagulation. However, such treatment requires thermal destruction of the neovascular tissue, and is accompanied by full-thickness retinal damage, as well as damage to medium and-large choroidal vessels. Further, the subject is left with an atrophic scar and visual scotoma. Moreover, recurrences are common, and visual prognosis is poor.

Developing strategies have sought more selective closure of the blood vessels to preserve the overlying neurosensory retina. One such strategy is photodynamic therapy, which relies on low intensity light exposure of photosensitized tissues to produce photochemical effects. Photosensitizing dyes are preferentially retained in tumors and neovascular tissue, which allows for selective treatment of the pathologic tissue. As a result of the invention, PDT may be used to cause vascular occlusion in tumors by damaging endothelial cells, as well as a direct cytotoxic effect on tumor cells.

Photodynamic therapy of conditions in the eye characterized by neovascularization has been attempted over the past several decades using the conventional porphyrin derivatives such as hematoporphyrin derivative and Photofrin porfimer sodium. Problems have been encountered in this context due to interference from eye pigments. In addition, phthalocyanine has been used in photodynamic treatment.

A newer photosensitizer, a member of the group designated "green porphyrins", is in the class of compounds called benzoporphyrin derivatives (BPD). This photosensitizer has also been tested to some extent in connection with ocular conditions. For example, Schmidt, U. et al. described experiments using BPD coupled with low density lipoprotein (LDL) for the treatment of Greene melanoma (a non-pigmented tumor) implanted into rabbit eyes and achieved necrosis in this context (*IOVS* (1992) 33:1253 Abstract 2802). This abstract also describes the success of LDL-BPD in achieving thrombosis in a corneal neovascularization model. The corneal tissue is distinct from that of the retina and choroid.

The present applicants have described treating choroidal neovascularization using LDL-BPD in several abstracts published Mar. 15, 1993. These abstracts include those by Schmidt-Erfurth, U. et al. (abstract 2956); by Haimovici, R. et al. (abstract 2955); and by Walsh, A. W. et al. (abstract 2954). In addition, Lin, S. C. et al. described photodynamic closure of choroidal vessels using liposomal BPD in (abstract 2953). All of the foregoing are published in *IOVS* (1993) 34:1303. An additional abstract of the present applicants describing LDL-BPD to inhibit choroidal neovasculature is by Moulton, R. S. et al. (abstract 2294), *IOVS* (1993) 34:1169.

The green porphyrins offer advantages in their selectivity for neovasculature. The present applicants have further determined that coupling of the green porphyrins to a carrier such as LDL or as contained in a liposomal formulation provides an advantageous delivery method for the drug to the desired ocular location.

DISCLOSURE OF THE INVENTION

The invention is directed to diagnosis and treatment of certain conditions of the eye using photodynamic methods and employing green porphyrins as the photoactive compounds. The green porphyrins of the invention are described in U.S. Pat. Nos. 4,883,790; 4,920,143; 5,095,030; and 5,171,749, the entire contents of which are incorporated herein by reference. These materials offer advantages of selectivity and effectiveness when employed in protocols directed to the destruction of unwanted ocular neovasculature, especially in the choroid.

Accordingly, in one aspect, the invention is directed to a method to treat conditions of the eye characterized by unwanted neovasculature, which method comprises administering to a subject in need of such treatment an amount of a liposomal formulation of green porphyrin that will localize in said neovasculature; and irradiating the neovasculature with light absorbed by the green porphyrin.

In another aspect, the invention is directed to a method to treat conditions of the choroid characterized by unwanted neovascularization, such as AMD, which method comprises administering to a subject in need of such treatment an amount of a green porphyrin that will localize in the neovascularized choroid; and irradiating the choroid with light absorbed by the green porphyrin.

In still another aspect, the invention is directed to a method to treat age-related macular degeneration (AMD) which method comprises administering to a subject in need of such treatment an amount of green porphyrin that will localize in the choroid and irradiating the choroid with light absorbed by the green porphyrin.

MODES OF CARRYING OUT THE INVENTION

Figure 1:
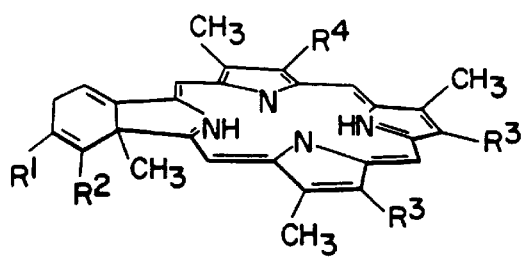
FIG. 1 shows preferred forms of the-green porphyrins useful in the methods of the invention.

In general, the green porphyrin is of a formula shown in FIG. 1 or a mixture thereof.

Referring to FIG. 1, in preferred embodiments each of $R^1$ and $R^2$ is independently selected from the group consisting of carbalkoxyl (2–6C), alkyl (1–6C), arylsulfonyl (6–10C), cyano and —CONR$^5$CO wherein R$^5$ is aryl (6–10C) or alkyl (1–6C); each R$^3$ is independently carboxyl, carboxyalkyl (2–6C) or a salt, amide, ester or acylhydrazone thereof or is alkyl (1–6C); R$^4$ is —CH=CH$_2$ or —CH(OR$^{4'}$) CH3 wherein R$^{4'}$ is H, or alkyl (1–6C) optionally substituted with a hydrophilic substituent. Especially preferred also are green porphyrins of the formula shown in FIGS. 1–3 or 1–4 or mixtures thereof.

More preferred embodiments are those wherein the green porphyrin is of the formula shown in FIGS. 1–3 or 1–4 or a mixture thereof and wherein each of R$^1$ and R$^2$ is independently carbalkoxyl (2–6C); one R$^3$ is carboxyalkyl (2–6C) and the other R$^3$ is an ester of a carboxyalkyl (2–6C) substituent; and R$^4$ is —CH=CH$_2$ or —CH(OH)CH$_3$.

Figures 1, 2:
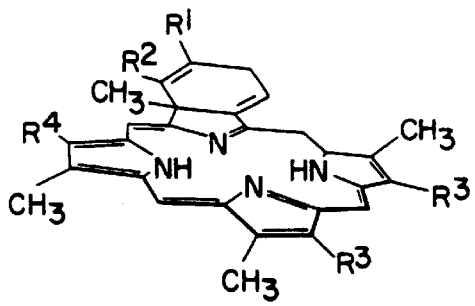
Figures 1, 2, 3:
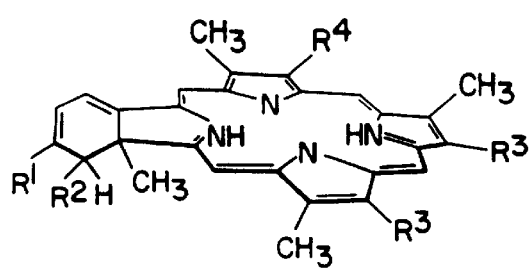
Figures 1, 2, 3, 4:
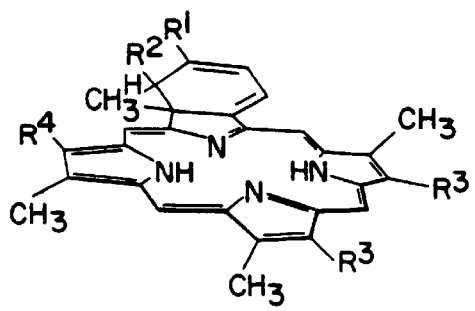
Figures 1, 2, 3, 4, 5:
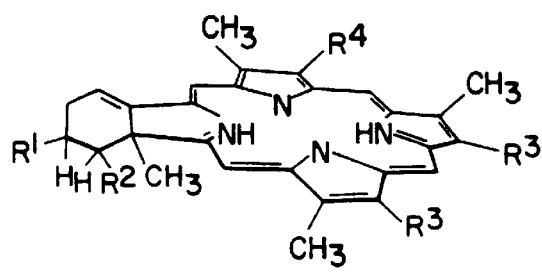
Figures 1, 2, 3, 4, 5, 6:
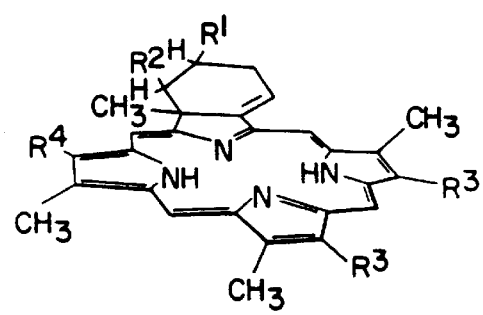

Still more preferred are embodiments wherein green porphyrin is of the formula shown in FIGS. 1–3 and wherein R$^1$ and R$^2$ are methoxycarbonyl; one R is —CH$_2$CH$_2$COOCH$_3$ and the other R$^3$ is —CH$_2$CH$_2$COOH; and R$^4$ is —CH=CH$_2$; i.e., BPD—MA.

The green porphyrin is formulated into a delivery system that delivers high concentrations to the target tissue. Such formulations may include coupling to a specific binding ligand which may bind to a specific surface component of the neovasculature or by formulation with a carrier that delivers higher concentrations to the target tissue.

In one preferred embodiment, the green porphyrin is prepared as a liposomal formulation. Liposomal formulations are believed to deliver the green porphyrin selectively to the low-density lipoprotein component of plasma which, in turn acts as a carrier to deliver the active ingredient more effectively to the neovasculature. Increased numbers of LDL receptors have been shown to be associated with neovascularization, and by increasing the partitioning of the green porphyrin into the lipoprotein phase of the blood, it appears to be delivered more efficiently to the neovasculature. Green porphyrins, and in particular BPD—MA, strongly interact with such lipoproteins. LDL itself can be used as a carrier, but LDL is considerably more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins involving lipocomplexes, including liposomes, are described in U.S. Pat. No. 5,214,036 and in U.S. Ser. No. 07/832,542 filed Feb. 5, 1992, the disclosures of both of these being incorporated herein by reference. Liposomal BPD can also be obtained from Quadra Logic Technologies, Inc., Vancouver, British Columbia.

When injected intravenously, BPD—MA is cleared from the bloodstream with a half-life of about 10–30 minutes, with the highest tissue levels being reached in about three hours after administration by injection and declining rapidly in the first 24 hours. BPD—MA is cleared primarily via bile and feces (60%), with only 4% being cleared via the kidneys and urine. Thus, skin photosensitivity occurs with BPD—MA only transiently, with minimal reactivity after 24 hours in in vivo models.

The green porphyrin can be administered in any of a wide variety of ways, for example, orally, parenterally, or rectally. Parenteral administration, such as intravenous, intramuscular, or subcutaneous, is preferred. Intravenous injection is especially preferred.

The dose of green porphyrin can vary widely depending on the tissue to be treated; the physical delivery system in which it is carried, such as in the form of liposomes; or whether it is coupled to a target-specific ligand, such as an antibody or an immunologically active fragment.

It should be noted that the various parameters used for effective, selective photodynamic therapy in the invention are interrelated. Therefore, the dose should also be adjusted with respect to other parameters, for example, fluence, irradiance, duration of the light used in photodynamic therapy, and time interval between administration of the dose and the therapeutic irradiation. All of these parameters should be adjusted to produce significant damage to neovascular tissue without significant damage to the surrounding tissue. Typically, the dose of green porphyrin used is within the range of from about 0.1 to about 20 mg/kg, preferably from about 0.15–2.0 mg/kg, and even more preferably-from about 0.25 to about 0.75 mg/kg.

Specifically, as the green porphyrin dose is reduced from about 2 to about 1 mg/kg, the fluence required to close choroidal neovascular tissue tends to increase, for example, from about 50 to about 100 Joules/cm$^2$.

After the photosensitizing green porphyrin has been administered, the neovascular tissue or tumor being treated in the eye is irradiated at the wavelength of maximum absorbance of the green porphyrin, usually between about 550 and 695 nm. A wavelength in this range is especially preferred for enhanced penetration into bodily tissues.

As a result of being irradiated, the green porphyrin in its triplet state is thought to interact with oxygen and other compounds to form reactive intermediates, such as singlet oxygen, which can cause disruption of cellular structures. Possible cellular targets include the cell membrane, mitochondria, lysosomal membranes, and the nucleus. Evidence from tumor and neovascular models indicates that occlusion of the vasculature is a major mechanism of photodynamic therapy, which occurs by damage to endothelial cells, with subsequent platelet adhesion, degranulation, and thrombus formation.

The fluence during the irradiating treatment can vary widely, depending on type of tissue, depth of target tissue, and the amount of overlying fluid or blood, but preferably varies from about 50–200 Joules/cm$^2$.

The irradiance typically varies from about 150–900 mW/cm$^2$, with the range between about 150–600 mW/cm$^2$ being preferred. However, the use of higher irradiances may be selected as effective and having the advantage of shortening treatment times.

The optimum time following green porphyrin administration until light treatment can vary widely depending on the mode of administration, the form of administration such as in the form of liposomes or as a complex with LDL, and the type of target tissue. As a specific example, an exposure time of 1–20 minutes is often appropriate for retinal neovascular tissue, about 120 minutes for choroidal neovascular tissue, and up to about three hours for tumors. Thus, effective vascular closure generally occurs at times in the range of about one minute to about three hours following administration of the green porphyrin.

The time of light irradiation after administration of the green porphyrin may be important as one way of maximizing the selectivity of the treatment, thus minimizing damage to structures other than the target tissues. For a primate, it is believed that the green porphyrin begins to reach the retinal vasculature by about 7–15 seconds following administration. Typically, the green porphyrin persists for a period of about 5–15 minutes, depending on the dose given. Treatment within the first five minutes following administration of the green porphyrin should generally be avoided to prevent undue damage to retinal vessels still containing relatively high concentrations of the green porphyrin.

Clinical examination and fundus photography typically reveal no color change immediately following photodynamic therapy, although a mild retinal whitening occurs in some cases after about 24 hours. Closure of choroidal neovascularization, however, is preferably confirmed histologically by the observation of damage to endothelial cells. Vacuolated cytoplasm and abnormal nuclei can become apparent as early as 1–2 hours following photodynamic therapy, with disruption of neovascular tissue typically becoming more apparent by about 24 hours after light treatment. Associated damage to the retinal pigment epithelium (RPE), pyknotic nuclei in the outer nuclear layer, and loss of photoreceptors may also be observed. However, the inner retina usually appears relatively undamaged, as shown by control studies using photodynamic therapy with BPD—MA on a normal retina and choroid showing no damage to large choroidal and retinal vessels.

Closure can usually be observed angiographically by about 40 seconds to a minute in the early frames by hypofluorescence in the treated areas. During the later angiographic frames, a corona of hyperfluorescence begins to appear and then fills the treated area, possibly representing leakage from the adjacent choriocapillaris through damaged retinal pigment epithelium in the treated area. Large retinal vessels in the treated area perfuse following photodynamic therapy, but tend to demonstrate late staining.

Minimal retinal damage is generally found on histopathologic correlation and is dependent on the fluence and the time interval after irradiation that the green porphyrin is administered. Histopathologic examination usually reveals vessel remnants in the area of choroidal neovascular tissue, but the retinal vessels typically appear normal. Further, there is no indication of systemic toxicity, and cutaneous photosensitization does not appear to develop.

As a result of the invention, photodynamic therapy can be used more selectively, relying on the low intensity light exposure of green porphyrins that have become localized within vascular tissue. Complications, such as hemorrhage, are not noted with the invention method. Thus, photodynamic therapy with a green porphyrin appears to have broad application to clinical ophthalmology in treating such diseases as age-related macular degeneration, neovascular glaucoma, and persistent disc neovascularization in diabetic retinopathy.

The following examples are to illustrate but not to limit the invention.

EXAMPLE 1
Control of Experimental Choroidal Neovascularization Using PDT with BPD—MA/LDL at Low Irradiance Cynomolgus monkeys weighing 3–4 kg were anesthetized with an intramuscular injection of ketamine hydrochloride (20 mg/kg), diazepam (1 mg/kg), and atropine (0.125 mg/kg), with a supplement of 5–6 mg/kg of ketamine hydrochloride as needed. For topical anesthesia, proparacaine (0.5%) was used. The pupils were dilated with 2.5% phenylephrine and 0.8% tropicamide.

Choroidal neovascularization was produced in the eyes of the monkeys using a modification of the Ryan model, in which burns are placed in the macula, causing breaks in Bruch's membrane, with a Coherent Argon Dye Laser 4920, Coherent Medical Laser, Palo Alto, Calif. (Ohkuma, H. et al. Arch. Ophthalmol. (1983) 101:1102–1110; Ryan, S. J. Arch Ophthalmol (1982) 100:1804–1809). Initially, a power of 300–700 mW for 0.1 seconds was used to form spots of about 100 $\mu$m, but improved rates of neovascularization were obtained with 50$\mu$ spots formed using a power of about 300–450 mW for 0.1 second.

The resulting choroidal neovascularizations were observed by (1) fundus photography (using a Canon Fundus CF-60Z camera, Lake Success, Long Island, N.Y.); (2) by fluorescein angiography (for example, by using about 0.1 ml/kg body weight of 10% sodium fluorescein via saphenous vein injection); and (3) histologic examination by light and electron microscopy.

Immediately before use, BPD—MA was dissolved in dimethyl sulfoxide (Aldrich Chemical Co., Inc., Milwaukee, Wis.) at a concentration of about 4 mg/ml. Dulbeccos phosphate buffered salt solution (Meditech, Washington, D.C.) was then added to the stock to achieve a final BPD concentration of 0.8 mg/ml. Human low-density-lipoprotein (LDL) prepared from fresh frozen plasma was added at a ratio of 1:2.5 mg BPD—MA:LDL. The green porphyrin dye and dye solutions were protected from light at all times. After mixing, the dye preparation was incubated at 37° for 30 minutes prior to intravenous injection. The monkeys were then injected intravenously via a leg vein with 1–2 mg/kg of the BPD—MA complexed with LDL over a five-minute period, followed by a flush of 3–5 cc of normal saline.

Following this intravenous injection, the eyes of the monkeys were irradiated with 692 nm of light from an argon/dye laser (Coherent 920 Coherent Medical Laser, Palo Alto, Calif.), using a Coherent LDS-20 slit lamp. The standard fiber was coupled to larger 400 $\mu$m silica optical fiber (Coherent Medical Laser, Pal Alto, Calif.) to allow larger treatment spots as desired. Seventeen (17) areas of choroidal neovascularization were treated using a 1250 $\mu$m spot. Treatment spot sizes were confirmed at the treatment plane using a Dial caliper micrometer. Some areas of choroidal neovascularization were treated with several adjacent treatment spots to treat the whole area of choroidal neovascularization. One large choroidal neovascular membrane was treated with photodynamic therapy to the nasal half only.

The photodynamic irradiation treatments were carried out with a plano fundus contact lens (OGFA, Ocular Instruments, Inc., Bellvue, Mass.). Power was verified at the cornea by a power meter (Coherent Fieldmaster, Coherent, Auborn, Calif.). The fluence at each treatment spot was 50, 75, 100 or 150 Joules/cm$^2$. Initially, the irradiance was set at 150 mW/cm$^2$ to avoid any thermal effect but, as the experiment proceeded, the irradiance was increased to 300 mW/cm$^2$ or 600 mW/cm$^2$ to reduce the treatment duration time. The time interval between injection of the green porphyrin dye and the treatment irradiating step ranged from about 1 to about 81 minutes.

A number of different combinations of parameter values were studied and are summarized below in Table 1:

TABLE 1

| IRRADIANCE AT 150 mW/cm$^2$ | | | | | |
|---|---|---|---|---|---|
| Number of CNV Treated | Dye dose (mg/kg) | Fluence (J/cm$^2$) | Duration of Treatment (mins) | Time after Injection (mins) | Closure by Angiography |
| 2 | 2 | 50 | 5.6 | 18, 38 | 2/2 |
| 1 | 2 | 75 | 8.3 | 81 | 1/1 |
| 1 | 2 | 100 | 11.2 | 22 | 1/1 |
| 2 | 1 | 50 | 5.6 | 5, 30 | 0/2 |

TABLE 1-continued

IRRADIANCE AT 150 mW/cm$^2$

| Number of CNV Treated | Dye dose (mg/kg) | Fluence (J/cm$^2$) | Duration of Treatment (mins) | Time after Injection (mins) | Closure by Angiography |
|---|---|---|---|---|---|
| 3 | 1 | 100 | 11.2 | 1, 2 and 5 | 3/3 |
| 4 | 1 | 150 | 16.6 | 14–43 | 3/4 |

"Dye only" controls, which were exposed to dye but not to laser light, were examined in the areas of normal retina/choroid. Areas of choroidal neovascularization were examined angiographically and histologically. "Light only" controls were not performed, since the irradiances used for photodynamic therapy-were well below the levels used for clinical laser photocoagulation. (In a related experiment, a minimally detectable lesion using "light-only" required an irradiance of 37 W/cm$^2$, about 100 times the light levels used for photodynamic therapy.)

Following photodynamic therapy, the monkeys were returned to an animal care facility. No attempt was made to occlude the animals' eyes, but the room in which they were housed was darkened overnight.

The condition of the choroidal neovasculature was followed by fundus photography, fluorescein angiography, and histologic examination. In particular, the eyes of the monkeys were examined by fluorescein angiography acutely and at 24 hours after the photodynamic therapy was given. In some cases, follow-up by fluorescein angiography was performed at 48 hours and at one week, until the eyes were harvested and the animals killed at the following time points: acutely, at 24 hours, 48 hours, and 8 days following photodynamic therapy. Animals were sacrificed with an intravenous injection of 25 mg/mg Nembutal.

To perform the histologic examination, all eyes were enucleated under deep anesthesia and fixed overnight in modified Karnovsky's fixative, and then transferred to 0.1M phosphate buffer, pH 7.2 at 4° C. Both light microscopy and electron microscopy were used for these studies. For light microscopy, tissue samples were dehydrated, embedded in epon and serially sectioned at one micron. The sections were stained with tolnizin blue and examined with an Olympus photomicroscope. For electron microscopy, tissue samples were post-fixed in 2% osmium tetroxide and dehydrated in ethanol. Sections were stained with uranyl acetate in methanol, stained with Sato's lead stain, and examined with a Philips #CM 10 transmission electron microscope.

Using the low irradiance level of 150 mW/cm$^2$ to minimize any thermal component of the treatment, green porphyrin doses of 1–2 mg/kg of BPD—MA/LDL, and fluences of 50–150 Joules/cm$^2$, choroidal neovascularization was effectively closed. Using the higher 2 mg/kg dose effectively closed choroidal neovascularizations at even the lowest 50 Joules/cm$^2$ fluence. When the green porphyrin dose was decreased to decrease the damage to surrounding tissues to 1 mg/kg of BPD—MA/LDL, the fluence required to effectively close choroidal neovascular tissue increased to 100 Joules/cm$^2$. At 100 and 150 Joules/cm$^2$, the treated choroidal neovascular tissue was angiographically closed, as shown by hypofluorescence in the area of treatment.

Prior to photodynamic therapy, the areas of choroidal neovascularization exhibited a gray sub-retinal elevation that leaked profusely on fluorescein angiography. There was no apparent color change in the treated areas either during or immediately after photodynamic treatment. However, 24 hours after the irradiating step, there was mild retinal whitening in the treated areas.

Further fluorescein angiography showed hypofluorescence in the treated areas, with no apparent filling of the associated neovascular tissues. Retinal vessels within the treated areas were perfused, but stained later. A hyperfluorescent rim at the border of the treated area was apparent in the later frames of the angiograph, and the rim then progressed to fill the treated area. Although mild staining of retinal vessels was noted angiographically, no complications, such as serous retinal detachment or hemorrhage, were noted.

On histopathologic examination of the 2 mg/kg dose samples, there was marked disruption of the treated choroidal neovascular tissue with disrupted endothelial cells. The choriocapillaris was also occluded. Although large choroidal vessels were unaffected, extravasated red blood cells were noted in the choroid. Retinal pigment epithelium (RPE) damage was noted as well with vacuolated cells, with the outer nuclear layer demonstrating pyknotic nuclei and disrupted architecture. No histologic abnormality of the retinal vessels was seen.

Histopathologic examination of the 1 mg/kg dose samples showed damage to endothelial cells in the choroidal neovascular tissue, with abnormal nuclei and disrupted cytoplasm in the endothelial cells. The lumens of the vessels in the choroidal neovascular tissue were occluded by fibrin acutely and were closed by 24 hours after treatment. Closure of the choriocapillaris was also noted. At 24 hours, the retinal pigment epithelium (RPE) appeared abnormal with vacuolated cytoplasm. Pyknotic nuclei in the inner and outer layer indicated damage secondary to the laser injury used to induce the neovascularization in this model. Retinal vessels appeared to be undamaged.

Choroidal neovascular tissue that was treated and followed for eight days showed persistent closure, as shown by hypofluorescence in the early frames of the angiogram. Histologically, the treated areas demonstrated degraded vessel lumens empty of debris. The choriocapillaris was sparse but patent in the treated area. In contrast, areas of choroidal neovascularization not treated by photodynamic therapy demonstrated branching capillaries between Bruch's membrane and the outer retina.

No adverse effects of photodynamic therapy with the green porphyrin were noted. There was no associated serous retinal detachment, retinal or sub-retinal hemorrhage, or post-treatment inflammation. Further, no adverse systemic effects of the dye administration were noted. However, the low irradiance forced treatment times to be long—about 16.6 minutes to yield 150 Joules/cm$^2$.

EXAMPLE 2

Control of Experimental Choroidal Neovascularization Using PDT with BPD—MA/LDL at Higher Irradiances To make clinical treatments shorter, additional experiments were performed using higher irradiance values. Experience with higher irradiance indicated that no thermal damage would take place with irradiances as high as 1800 mW/cm$^2$. Moulton et al., "Response of Retinal and Choroidal Vessels to Photodynamic Therapy Using Benzoporphyrin Derivative Monoacid", *IOVS* 34, 1169 (1993), Abstract 2294–58. Therefore, irradiances of 300 mW/cm$^2$ and 600 mW/cm$^2$ were also used to treat choroidal neovascular tissue in accordance with the procedures described in Example 1. The results showed that shortened treatment times effectively closed the choroidal neovascular tissue, as indicated below in Table 2.

TABLE 2

IRRADIANCE OVER 150 mW/cm²

| Dye Number of CNV Treated | Flu-dose (mg/kg) | Irra-ence (J/cm²) | tion of diance (mW/cm²) | Dura-after Treat-ment (mins) | Time Closure Injec-tion (mins) | by Angio-graphy |
|---|---|---|---|---|---|---|
| 2 | 1 | 150 | 300 | 8.3 | 5, 53 | 2/2 |
| 2 | 1 | 150 | 600 | 4.7 | 22, 69 | 2/2 |

Occlusion of the choroidal neovascular tissue and subjacent choriocapillaris was observed, as well as damage to the retinal pigment epithelium and outer retina.

EXAMPLE 3
Control of Experimental Choroidal Neovascularization Using PDT with BPD—MA Liposomes The following experiment of photodynamic therapy using a liposomal preparation of BPD—MA was conducted to determine the optimal time interval after intravenous injection as a bolus of the BPD—MA over about 20 seconds, followed by a 3–5 cc saline flush, to begin the irradiating step. Choroidal neovascularization in cynomolgus monkeys was treated to demonstrate efficacy of the photodynamic therapy. Normal choroid tissue was treated to assess relative damage to adjacent tissues.

The monkeys were initially injected with a green porphyrin dose of 1 mg/kg. At predetermined time intervals following this injection, the eyes of the monkeys were irradiated with an irradiance of 600 mW/cm², and a fluence of 150 J/cm². The irradiating light was from an argon/dye laser (Coherent 920 Coherent Medical Laser, Palo Alto, Calif.) equipped with a 200 micron fiber adapted through a Laser-Link (Coherent Medical Laser) and a split lamp delivery system (Coherent). Other than these differences, the eye membranes were treated in the same manner as described in Example 1. All areas of treated choroidal neovasculature for all time points after the liposomal BPD—MA injection showed whitening of the retina and early hypofluorescense on fluorescein angiography when measured one week after treatment. On histology, there was evidence of partial closure of choroidal neovasculature at the early time points, no effect at mid-time points, and more effective closure at late irradiation time points, e.g., at 80 and 100 minutes.

The normal choroid treated with the same parameters showed whitening of the retina, early hypofluorescence at all time points, and histologic evidence of choriocapillaris (c—c) accompanied by damage to the choroid and retina, particularly at early time points.

EXAMPLE 4
Using PDT with BPD—MA Liposomes at Lower Green Porphyrin Doses Using the general procedure of Example 1, additional experiments were performed using the intravenous injection of liposomal BPD—MA at doses of 0.25, 0.5 and 1 mg/kg. Photodynamic therapy was performed with an irradiance of 600 mW/cm², a fluence of 150 J/cm², and a treatment duration of four minutes, nine seconds.

The effects of treatment were assessed by fundus photography and fluorescein angiography, and then confirmed by light and electron microscopy. Photodynamic therapy of normal choroid tissue demonstrated the effect on adjacent structures, such as the retina, while the treatment of choroid neovascular tissue demonstrated efficacy.

Table 3 below describes the lesions produced on normal choroids by administration of 0.5 mg/kg BPD—MA at time points ranging from 5 to 60 minutes:

TABLE 3

0.5 mg/kg, NORMAL CHOROID

| Time after injection (min) | Fluorescein Angiography | Histology |
|---|---|---|
| 5 | Hypofluorescence | c-c and large choroidal vessel closure; outer and inner retina damage. |
| 20 | Hypofluorescence; retinal vessels - normal | cc closure; damage to outer retina |
| 40 | Mild early hypofluorescence | cc open (not center of lesion); outer retina damage |
| 60 | Early hypofluorescence; less than the 20-minute lesion described above | cc closed; outer retina damage; inner retina fairly good. |

When 0.5 mg/kg BPD—MA was also used to treat choroidal neovasculature under the same conditions, marked hypofluorescence corresponding to closure of choroid neovasculature was exhibited in areas irradiated at times of 5, 20 and 40 minutes after injection. When 50 minutes after injection were allowed to elapse before photodynamic irradiation was begun, there was less hypofluorescence and presumably less effective closure.

The study was then repeated with the green porphyrin dose decreased to 0.25 mg/kg. Table 4 below describes the lesions produced on normal choroids by treatments with 0.25 mg/kg, 600 mW/cm², and 150 J/cm² at time points ranging from 5 to 60 minutes:

TABLE 4

0.25 mg/kg, NORMAL CHOROID

| Time after injection (min) | Fluorescein Angiography | Histology |
|---|---|---|
| 10 | Early hypofluorescence | c-c closure; choroidal vessel - normal; RPE damaged; retinal vessels - normal; mild damage to outer retina |
| 20 | Early hypofluorescence | Same as 10-minute lesion above |
| 40 | Faint early hypofluorescence; late staining | Patchy cc closure; less damage to RPE and outer retina |
| 60 | Not demonstrated | No effect on cc; mild vacuolization of RPE |

When the above study was repeated using the same green porphyrin dose of 0.25 mg/kg and irradiance of 600 mW/cm², but with a reduced fluence of 100 J/cm², the same angiographic and histologic pattern was exhibited as described above. However, cc was open in the 40-minute lesion.

In the last portion of these experiments, a green porphyrin dose of 0.25 mg/kg was used to treat experimental choroidal neovascularization with an irradiance of 600 mW/cm² and a fluence of 150 J/cm$^2$ at elapsed time points ranging from 5 to 100 minutes. This combination of conditions caused effective cc closure with only minimal damage to the outer retina. The results are shown in Table 5 below:

TABLE 5

0.25 mg/kg, PDT over CNV

| Time after injection (min) | Fluorescein Angiography | Histology |
| --- | --- | --- |
| 5 | Early hypofluorescence | Partially closed CNV; c-c closed; damage to inner retina |
| 20 | Early hypofluorescence; less than the 5-minute lesion | CNV - open vessel, fibrin and clots; inner retina looks fine |
| 30 | Some hypofluorescense next to CNV | Minimal effect on CNV |
| 40 | Hypofluorescence; questionable change compared to previous reaction | Minimal effect on CNV |
| 60 | Hypofluorescence | Minimal effect on CNV |
| 80 | Hypofluorescence | Partial closure of CNV; retina over CNV looks intact |
| 100 | Hypofluorescence | CNV partially closed |

Thus, fluorescein angiography and histopathology in the above series of experiments demonstrated early hypofluorescence at early time points. Further, the histopathology study showed partial CNV closure at all time points after injection using 80 and 100 minutes as the post-injection interval before the irradiating treatment.

In summary, acceptable destruction of choroidal neovascular tissue at all tested doses of BPD—MA was shown by fluorescein angiography and histology. However, the lower doses appeared to increase selectivity, as assessed by treatment of a normal choroid. Effective choriocapillaris closure in normal choroids with minimal retinal damage was produced by irradiating at a time about 10 minutes, 20 seconds after injection of the green porphyrin at a dose of 0.25 mg/kg. By adjusting the dose, the time of irradiation after green porphyrin injection, and fluence, one can improve even further the selectivity of the green porphyrin. However, the liposomal preparation of BPD—MA was clearly demonstrated to be a potent photosensitizer.

EXAMPLE 5

Additional Data Using Liposomal BPD

Using the techniques of Examples 1–4, a total of 61 areas of experimental CNV in 9 monkeys were treated with PDT using BPD—MA. Effective CNV closure was demonstrated by fluorescein angiography at all tested dye doses: 1, 0.5, 0.375, and 0.25 mg/kg. The lower the dose, the shorter the time interval after dye injection in which laser irradiation produced CNV closure.

The fundus appearance was unchanged immediately after treatment, and only slight deep retinal whitening corresponding to the laser irradiation spot appears 24 hours later. CNV closure was determined angiographically at 24 hours by early hypofluorescence corresponding to the treated area. As the angiogram progressed most lesions demonstrated staining starting at the periphery of the lesion.

Table 6 summarizes the effect of PDT on CNV, using different dye doses and variable treatment times after dye injection. PDT using a dye dose of 1 mg/kg was performed over 7 membranes in 1 monkey. Laser irradiation was performed at each of the following times after dye injection: 5, 20, 40, 60, 80, 100 and 120 minutes. CNV closure was induced in all lesions when irradiation was performed 5–100 minutes after dye injection.

TABLE 6

Angiographic Closure of CNV

| Dye Dose mg/kg | No. Lesions CNV | Time (min) of R after dye injection | CNV closure |
| --- | --- | --- | --- |
| 1 | 7 | 5–100 | 6/7 |
| | | >100 | 0/1 |
| 0.5 | 11 | <60 | 7/8 |
| | | 60–100 | 0/3 |
| 0.375 | 29 | <50 | 16/18 |
| | | 50–100 | 3/11 |
| 0.25 | 14 | <20 | 2/2 |
| | | 20–40 | 2/4 |
| | | 40–100 | 0/8 |

PDT using dye dose of 0.5 mg/kg was performed on 11 membranes in 2 monkeys, with laser irradiation at 10, 20, 30, 40, 50, 60, 80, 100 minutes after dye injection. PDT effect was assessed 24 hours after treatment. CNV closure was induced in 7/11 membranes, that were irradiated at 10, 20, 30, 40 and 50 minutes after dye injection. Only ½ membranes irradiated at 50 minutes after dye injection showed angiographic closure. The treatments performed 60 minutes and more after dye injection showed no angiographic closure of the membranes.

29 areas of CNV in 5 monkeys were treated with PDT using BPD—MA at dose of 0.375 mg/kg. All treated CNV membranes were assessed angiographically at 24 hours. As indicated in Table 6, ⅞ CNV irradiated within 50 minutes after injection demonstrated angiographic closure. Only 3/11 membranes irradiated more than 50 minutes after dye injection demonstrated angiographic closure.

A dye dose of 0.25 mg/kg was found to be the threshold dose for PDT using a light dose of 150 J/cm$^2$ and 600 mW/cm$^2$. CNV closure was demonstrated in 2/2 membranes that were irradiated within 20 minutes after dye injection. Only 2/4 CNV irradiated 20–40 minutes after dye injection showed closure. No effect was demonstrated in the CNV that were irradiated more than 40 minutes after dye injection.

Histologic confirmation of CNV closure was evident at all tested dye doses: 1, 0.5, 0.375, and 0.25 mg/kg.

On light microscopy the closed CNV showed vessels packed with red blood cells (RBCs), occasional extravasated RBCs and pockets of fibrin within the tissue as well as in the subretinal space. Most of the stromal cells appeared undamaged.

On electron microscopy the closed vessels appeared packed with RBCs and platelets. The endothelial cells were missing or severely damaged. Extravasated RBCs and occasional white blood cells (WBCs) were found near the vessel remnants. At 0.25 mg/kg the vessels were packed with RBCs but the endothelial cells seemed to be surviving the treatment.

Treatment Selectivity

Treatment selectivity was investigated by performing PDT in normal retina/choroid using the same dye doses and time points of laser irradiation after dye injection. In most cases the closure of the choriocapillaris in normal choroid followed a similar time course as the closure of CNV. When PDT was performed using dye doses of 0.5, 0.375, 0.25 mg/kg, the retinal structure was well preserved. In none of the cases were retinal detachment or hemorrhage observed reducing the dye dose resulted in more selective closure of the choriocapillaris with minimal damage to the adjacent tissues. RPE cells were typically damaged at all dye doses.

The assessment of the damage to the retina and choroid was graded according to the histologic findings for the retina/choroid at different levels, as follows:

Grade 1: RPE only or RPE+slight photoreceptor changes+ occasional pyknosis in the ONL; with or without choriocapillaris (c—c) closure;

Grade 2: Choriocapillaris closure+RPE+photoreceptors+ 10–20% pyknosis in the ONL;

Grade 3: C-c closure+RPE+photoreceptors+ONL pyknosis>50%;

Grade 4: C-c closure+RPE+photoreceptors+ONL pyknosis>50%;

Grade 5: C-c closure+RPE+photoreceptors+ONL pyknosis>50%+choroidal vessel damage or retinal vessel or inner retinal damage;

A total of 38 PDT spots were placed in normal retina/choroid. The treatment parameters and the degree of effect are summarized in Table 7.

TABLE 7

PDT effect on normal retina/choroid

| Dye Dose | Time (min) of R after dye injection | No. Lesions | No. of lesions per histologic grading | | | | |
|---|---|---|---|---|---|---|---|
| | | | 1 | 2 | 3 | 4 | 5 |
| 1 mg/kg | <60* | 2 | | | | | 2 |
| | 60–100* | 3 | | | | 3 | |
| 0.5 mg/kg | <20 | 1 | | | | | 1 |
| | 20–60 | 3 | | | | 3 | |
| 0.375 mg/kg | <20 | 3 | 1 | 1 | 1 | | |
| | 20–50 | 9 | 2 | 4 | 2 | 1 | |
| | 50–100 | 11 | 1 | 5 | | 5 | |
| 0.25 mg/kg | <20 | 1 | 1 | | | | |
| | 20–40 | 1 | 1 | | | | |
| | 40–60 | 2 | 2 | | | | |

*The lesions irradiated at 40 and 120 minutes were not identified histologically.

PDT using a dye dose of 1 mg/kg led to damage of both inner and outer retina. The early treatments (5 and 20 minutes after dye injection) demonstrated grade 5 effect with damage to the inner retina, and lesions induced 60 minutes and more after dye injection showed a grade 4 effect.

At 0.5 mg/kg, only the lesion irradiated 5 minutes after dye injection demonstrated damage to the inner retina (grade 5). Lesions irradiated at 20 minutes and later did not affect the inner retina, but showed pyknosis in the outer nuclear layer (ONL), vacuolization and disorganization of the photoreceptors' inner and outer segments, and damage to the RPE (grade 4).

At 0.375 mg/kg, ⅔ lesions irradiated 10 minutes after dye injection showed some congestion of the small retinal vessels, but the inner nuclear layer (INL) was preserved. Lesions applied 20 minutes and later after dye injection showed some pyknosis in the ONL, some vacuolization and disorientation of the photoreceptors' inner and outer segments, and damage to the RPE. Most lesions demonstrated damage of grade 1 or 2 or 3, with some lesions demonstrated grade 4 damage.

0.25 mg/kg was found to be a threshold dose for induction of choriocapillaris closure. This was achieved with almost no effect on the overlying retina. There was mild damage to some RPE cells, minimal swelling of photoreceptors, and a few pyknotic nuclei in the ONL.

"Dye only" control areas of normal retina/choroid showed no effect by fluorescein angiography or histologic examination.

What is claimed is:

1. A method of treating unwanted choroidal neovasculature in a shortened treatment time, the method comprising the steps of:

administering to a primate subject in need of such treatment an amount of a porphyrin dye sufficient to permit an effective amount to localize in the neovasculature; and irradiating the neovasculature with light at an irradiance of about 600 mW/cm$^2$, the light being absorbed by the porphyrin dye so as to occlude the neovasculature.

2. The method of claim 1, wherein the porphyrin is green porphyrin.

3. The method of claim 1, wherein the primate subject has age-related macular degeneration and occlusion of the neovasculature ameliorates symptoms of the age-related macular degeneration.

4. The method of claim 2, wherein the primate subject has a disorder selected from the group consisting of age related macular degeneration, ocular histoplasmosis syndrome and myopia, wherein occlusion of the neovasculature ameliorates the disorder.

5. A method of treating age-related macular degeneration in a primate subject having unwanted choroidal neovasculature in a shortened treatment time, the method comprising the steps of:

administering to the primate subject an amount of a green porphyrin dye sufficient to permit an effective amount to localize in the neovasculature; and irradiating the neovasculature with light at an irradiance of about 600 mW/cm$^2$, the light being absorbed by the porphyrin dye so as to occlude the neovasculature.

6. The method of claim 2, wherein the primate subject has age-related macular degeneration and occlusion of the neovasculature ameliorates symptoms of the age-related macular degeneration.

* * * * *